United States Patent
Garger, Jr. et al.

(10) Patent No.: US 6,300,057 B1
(45) Date of Patent: Oct. 9, 2001

(54) MELANINS WITH IMPROVED ABILITY TO INHIBIT HIV REPLICATION

(75) Inventors: Steven Garger, Jr., Vacaville; Saul Neidleman, Oakland, both of CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 08/796,822

(22) Filed: Feb. 6, 1997

(51) Int. Cl.[7] ............................... C12Q 1/70; C12Q 1/06; A01N 37/18
(52) U.S. Cl. ...................................... 435/5; 435/39; 514/2
(58) Field of Search ................. 514/2; 435/5, 39

(56) References Cited

U.S. PATENT DOCUMENTS

| | | | |
|---|---|---|---|
| 5,057,325 | * 10/1991 | Montefiori | 424/522 |
| 5,340,734 | * 8/1994 | della-Cioppa et al. | 435/212 |
| 5,466,592 | 11/1995 | della-Cioppa et al. | 435/212 |
| 5,486,351 | * 1/1996 | della-Cioppa et al. | |

FOREIGN PATENT DOCUMENTS

| | | |
|---|---|---|
| 0 455 175 A2 | 11/1991 | (EP) . |
| 0 491 644 A2 | 6/1992 | (EP) . |
| WO 91 17738 A | 11/1991 | (WO) . |
| WO 92 00373 A | 1/1992 | (WO) . |
| WO 94 12644 A | 6/1994 | (WO) . |
| WO 96 25920 A | 8/1996 | (WO) . |

OTHER PUBLICATIONS

Yasunobu, et al., "The Oxidation of Tyrosine–containing Peptides by Tyrosinase", *The Journal of Biological Chemistry*, 234(12):3291–3295 (1959).

Mitsuya et al.; "3–azido–3–deoxythymidine (BW A509U): an antiviral . . . "; PNAC; vol. 82; pp. 7096–7100, 1985.*

Montefiori, et al, "Selective antiviral activity of synthetic . . . " Antiviral Research 15:11–26, 1991.*

Yarchoan, et al. : Correlations between the in vitro and in vivo . . . : J. Enz. Inh.; vol. 6: pp. 99–111, 1992.*

Gait, et al. : Progress in anti–HIV structire–based drug design: TIBTECH: vol. 13: pp. 430–438, Oct. 1995.*

Candia, et al., "Inhibition of HIV Replication and Cytopathicity In Vitro by Synthetic Soluble Melanins," 6th International Conference On Aids (1990), p. ThA. 228 XP002069206, see the whole document.

Crippa, et al., "Chemistry of Melanins," *The Alkaloids* 36:253–322 (1989).

Faraldi et al., "Neuromelanin Overload and Nigral Degeneration in AIDS," *Modern Pathology* 7(1):138A (1994) XP002069209, see the whole document.

Haseltine, W.A. "Development of Antiviral Drugs for the Treatment of Aids: Strategies and Prospects," *Journal of Acquired Immune Deficiency Syndromes* 2:311–334 (1989).

Ito, et al., "Incorporation of Sulfhydryl Compounds into Melanins in Vitro," *Biochim. Biophys. Acta Ser. Gen. Subjects* 964(1):1–7 (1988) XP002069208, see p. 2, column 2, paragraph 2—p. 3, column 2, paragraph 1; figure 2; table 3.

Mohan, P. and Baba, M., "Sulfonic Acid Derivatives as Selective Anti–HIV–1 Agents," *Drugs of the Future* 18(4):351–358 (1993).

(List continued on next page.)

Primary Examiner—Hankyel T. Park
(74) Attorney, Agent, or Firm—Albert P. Halluin; Thomas Gallegos; Viola T. Kung

(57) ABSTRACT

Novel enzymatically produced melanins are described that are useful in the treatment of HIV infection. The novel remanins are optionally modified to contain chemical moieties such as halogens, sulfates, or sulfonyl groups. Additionally, the novel enzymatically synthesized melanins may be modified, or further modified, by chemical oxidation.

30 Claims, 1 Drawing Sheet

OTHER PUBLICATIONS

Figure 1:
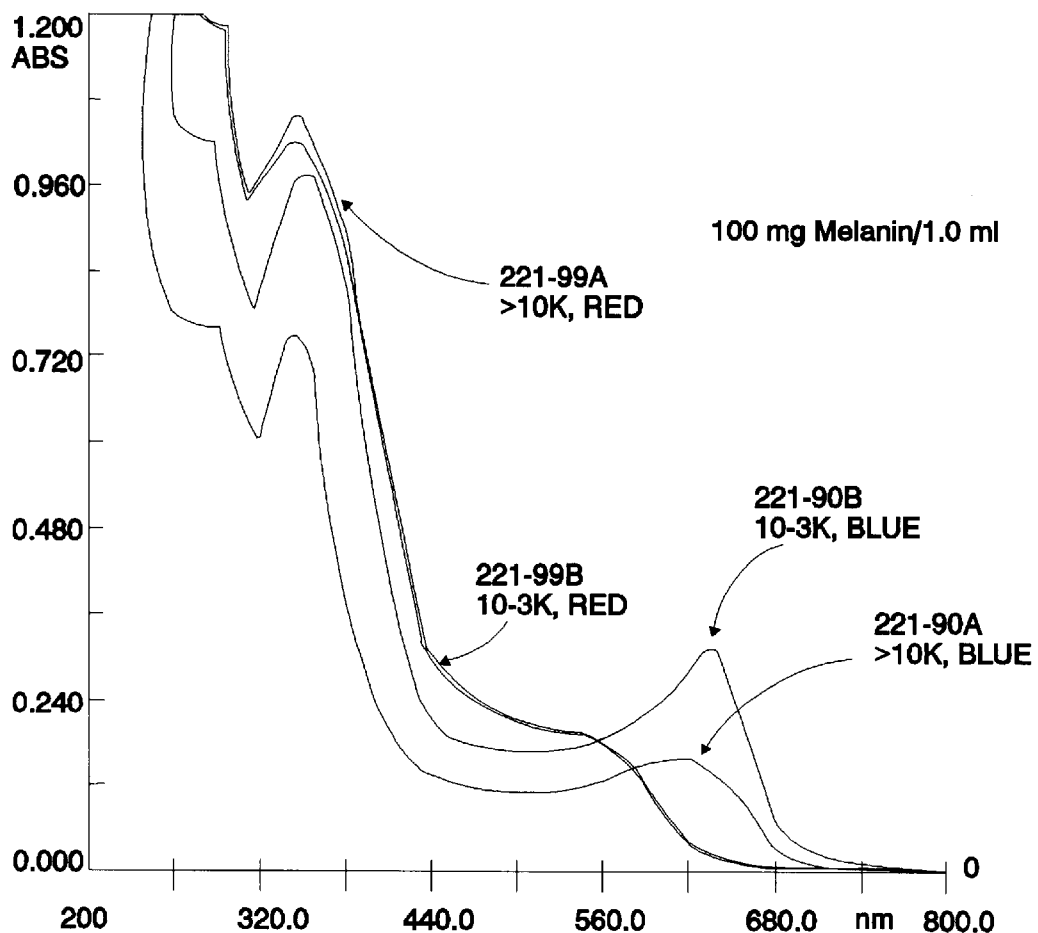

Montefiori, et al., "Evaluation of Antiviral Drugs and Neutralizing Antibodies to Human Immunodeficiency Virus by a Rapid and Sensitive Microtiter Infection Assay," *Journal of Clinical Microbiology* 26(2):231–235 (1988).

Montefiori, et al., "Inhibition of Human Immunodeficiency Virus Type 1 Replication and Cytopathicity by Synthetic Soluble Catecholamine Melanins In Vitro," *Biochem. Biophys. Res. Comm.* 168(1):200–205 (1990) XP002069204, see p. 202, paragraph 2—p. 204, paragraph 3; figures 1–3.

Montefiori, et al., "Selective antiviral activity of synthetic soluble L–tyrosine and L–dopa melanins against human immunodeficiency virus in vitro," *Antiviral Res.* 15(1):11–25 (1991) XP002069205, see p. 16, paragraph 2—p. 23, paragraph 1; figures 3–6; table 1.

Moriya, et al., "A New Candidate for an Anti–HIV–1 Agent: Modified Cyclodextrin Sulfate (mCDS71)," *J. Med. Chem.* 36:1674–1677 (1993).

Neidelman, S. and Geigert, J., "Biohalogenation: Principles, Basic Roles and Applications," Ellis Horwood Limited, Chichester, England, pp. 1–203 (1986).

Osawa, et al., "Synthesis of Sulfated Derivatives of Curdlan and Their Anti–HIV Activity," *Carbohydrate Polymers* 21:283–288 (1993).

Pezzella, et al., "Oxidative Polymerisation of 5,6–Dihydroxyindole–2–carboxylic Acid to Melanin: A New Insight," *Tetrahedron* 52(23):7913–7920 (1996) XP004103898, see the whole document.

Sidibe, et al., "Effects of serotonin and melanin on in vitro HIV–1 infection," *J. Biol. Regul. Homeostatic Agents* 10(1):19–24 (1996) XP002069207, see abstract, figures 1, 2.

Srivastava, et al., "Pentosan Polysulfate, a Potent Anti HIV and Anti Tumor Agent, Inhibits Protein Serine/Threonine and Tyrosine Kinases," *Molecular and Cellular Biochemistry* 120:127–133 (1993).

Tan, et al., "Sulfonic Acid Polymers are Potent Inhibitors of HIV–1 Induced Cytopathogenicity and the Reverse Transcriptases of Both HIV–1," *Biochemica et Biophysica Acta* 1181:183–188 (1993).

Toukairin, et al., "New Substances against Human Immunodeficiency Virus: Sulfated 5'–Nucleotidase Inhibitory Polyphenols," *Chem. Pharm. Bull.* 40(3):802–804 (1992) XP002069210, see the whole document.

Uryu, et al., "Synthesis of Anti–HIV Active Sulfated Polysaccharides and Sulfated Alkyl Oligosaccharides," *Carbohydrates and Carbohydrate Polymers, Analysis, Biotechnology, Modification, Antiviral, Biomedical and Other Applications*, Yalpani, M. ed., pp. 101–115 (1993).

Wilczok, et al., "Spectroscopic Studies of Chemically Modified Synthetic Melanins," *Archives of Biochemistry and Biophysics* 231(2):257–262 (1984).

Witvrouw, et al., "Activity of a Sulfated Polysaccharide Extracted from the Red Seaweed *Aghardhiella Tenera* Against Human Immunodeficiency Virus and Other Enveloped Viruses," *Antiviral Chemistry & Chemotherapy* 5(5):297–303 (1994).

Witvrouw, et al., "Antiviral Portrait Series: 4. Polysulfates as Inhibitors of HIV and Other Enveloped Viruses," *Antiviral Chemistry & Chemotherapy* 5(6):345–359 (1994).

\* cited by examiner

Ultraviolet Spectra of Selected Melanins

MELANINS WITH IMPROVED ABILITY TO INHIBIT HIV REPLICATION

1.0. FIELD OF THE INVENTION

The general field of this invention is therapeutic agents for combating viral infections. In particular, the present invention relates to the treatment of patients infected with human immunodeficiency virus (HIV) which causes Acquired Immuno Deficiency Syndrome (AIDS).

2.0. BACKGROUND OF THE INVENTION

Human immunodeficiency virus (HIV) has been determined to be the etiologic agent for acquired immunodeficiency syndrome (AIDS). The past decade has seen an unprecedented massive, worldwide research effort to discover effective therapies for HIV/AIDS costing billions of dollars that has only yielded limited success. Current therapeutic agents used during the treatment of chronic phase of HIV infection have not been particularly efficacious and are, at best, only able to slow the progress of infection. For example, several drugs have been identified which inhibit the replication of HIV in vitro (Haseltine, W. A., *J. Acquir. Immune Def. Syndr.,* 2:311–324, 1989) and nucleotide chain elongation inhibitors such as 3-azidothymidine (AZT) have received widespread acceptance for clinical use. However, the clinical efficacy of drugs like AZT has proven rather limited, and their use is further restricted by toxicity factors, and drug-resistant forms of the virus. Montefiori (U.S. Pat. No. 5,057,325), discovered that melanin produced by chemical oxidation when applied to HIV-infected cells in vitro exhibited anti-HIV activity.

Melanin is an omnibus term that describes a large family of natural and synthetic phenolic-quinonoid pigments of diverse origin and chemical nature. Natural melanins are generally differentiated by their origin; for example, bovine eye melanin, melanoma melanin and sepia melanin. They usually occur in the form of granular particles and are secretory products of pigment-producing cells, the melanocytes. Synthetic melanins are named after the compound from which they were prepared via chemical or enzymatic oxidation (e.g., d- and l-dopa., or 5,6-dihydroxyindole catechol melanin). In addition, melanins are classified according to their chemical structure into the insoluble black eumelanins (poly-5,6-indole quinones) and the alkali soluble red phaeomelanins (polydihydrobenzothiazines). The study of melanins has led to the discovery of a number of biosynthetic pathways. For example, melanins can be produced by the oxidation of its precursors such as l-dopa or tyrosine by the melanin-synthesizing enzyme, tyrosinase. Alternatively, melanin can be prepared chemically by the auto-oxidation of l-dopa or other substrates to melanin, in the presence of atmospheric oxygen (Wilczok et al., *Arch Biochem. Biophys.* 23:257, 1984). Additionally, melanin can be prepared by a variety of electrochemical and photochemical methods from which individual steps of the melanization processes are identified and characterized. See, Crippa, et al., (1989), supra. In this invention, melanins are produced in either aqueous or organic solutions, using the tyrosinase-mediated polymerization of tyrosine and tyrosine dipeptides and mixtures of both (della-Cioppa, et al., op. cit.). Tyrosine dipeptides have been previously used to produce melanins with tyrosinase; however, prior to the present invention, no one had recognized that such compounds may possess anti-viral activity. Thus, the presently disclosed anti-viral functions and modifications were never investigated (Yasunobu, et al., 1959).

Individuals infected with HIV (HIV-positive) may not develop symptoms of AIDS for years, but eventually the vast majority of HIV-positive patients develop AIDS. AIDS patients suffer from an overwhelming assault of diseases and have a poor prognosis for long term survival even when subjected to aggressive therapeutic regimens. Consequently, there is a compelling need to develop an effective anti-HIV therapy to either eliminate or arrest the progression of HIV infection and to prevent or treat AIDS.

3.0 SUMMARY OF THE INVENTION

To achieve this end, a first aspect of the present invention relates to a novel method for arresting HIV replication as a therapy for persons exposed to the HIV virus or testing HIV-positive, and for AIDS patients by administering an effective dose of melanin derived from the controlled enzymatic action of tyrosinase in conjunction with specific substrates or mixtures of substrates.

A second aspect of the invention relates to methods for the chemical polysulfation of enzymatically or non-enzymatically produced melanin to increase antiviral activity, as well as the sulfated or polysulfated melanin products of such methods.

A third aspect of the invention relates to methods for the chemical polyhalogenation of melanin with fluorine, chlorine, bromine and/or iodine to increase antiviral activity, as well as the halogenated melanin products of such methods.

A fourth aspect of the invention relates to the therapeutic use of melanins that have been modified by any combination of polysulfation, polysulfonation, and/or polyhalogenation.

A fifth aspect of the invention relates to melanins produced by enzymatic synthesis using defined substrates, and modified forms thereof, that have been purified by precipitation by reducing the pH of a melanin containing solution below about 7.0, and preferably below about pH 3.0, with a preferred pH of about 1.5.

A sixth aspect of the invention relates to melanin produced by enzymatic synthesis wherein said melanin is oxidized by hydrogen peroxide or another suitable chemical oxidizer.

A seventh aspect of the invention relates to melanin produced by enzymatic synthesis wherein said melanin is further purified by passage through a suitable molecular sieve to obtain melanin having a molecular size greater than or equal to about 10,000 daltons.

An eighth aspect of the invention relates to melanin produced by either chemical or enzymatic synthesis wherein said melanin is further modified to have chemical subgroups selected from the group consisting of sulfonyl, sulfate and halogen chemical groups, or any mixture thereof.

4.0 DESCRIPTION OF THE FIGURES

FIG. 1 shows ultraviolet spectra of blue green and red melanins as described in section 6.8.

5.0 DETAILED DESCRIPTION OF THE INVENTION

The present invention relates to methods of using modified melanins to treat HIV-positive patients and AIDS patients. In particular, synthetic melanins that have been produced using specifically identified dipeptide substrates (dipeptide-containing melanins), and/or a mixture of chemically modified dipeptides and tyrosine. In particular, it has been discovered that melanins which have been enzymatically produced using tyrosinase, or high specific-activity preparations thereof, in conjunction with selected dipeptide substrates have a significantly enhanced ability to hinder HIV replication in patients infected with HIV relative to melanins produced using l-tyrosine or L-DOPA as the sole or major substrate (Montefiori, et al., 1988, J. Clin. Mircobiol. 26:231–235). For the purposes of the present invention, high specific activity tyrosinase generally comprises at least about 550 dopachrome units of activity per mg protein, preferably at least about 750 units per mg, more preferably at least about 825 units per mg, and specifically at least about 900 units per mg protein. A particularly advantageous feature of high specific activity tyrosinase is that it may be used to synthesize melanins that incorporate reduced amounts of contaminating amino acid.

The presently described enzymatically produced dipeptide melanins, or oxidized forms thereof, also display enhanced anti-HIV activity relative to melanins produced using l-tyrosine monomers as a major substrate that have been modified by chemical oxidization.

Additionally, the therapeutic efficacy of the presently disclosed melanins is further increased by the chemical addition of one or more of the following chemical moieties: sulfate, sulfonyl, and halogen.

Polysulfates are able to block HIV replication in cell culture at concentrations as low as 0.01 µg/ml. Additionally, negligible host cell toxicity is observed at concentrations of 2.5 mg/ml which means that polysulfates have an in vitro selectivity index for blocking HIV replication of at least 250,000. This low toxicity is particularly preferred in instances where melanin is used during the treatment of individuals only suspected of HIV exposure, during pregnancy, or during the early (acute) phase of HIV infection.

Sulfated polysaccharides show significant differences in their in vitro anti-HIV activities, depending on the HIV virus type. This suggests that marked differences exist in the target molecules of different virus types with which polysulfates interact. A marked increase in anti-HIV-1 activity was observed with increasing molecular weight (MW), with an optimum at a MW of 10,000 and, with increasing degree of sulfation, as demonstrated using various samples of dextran sulfate prepared from dextran fractions with MW ranging from 1,000 to 500,000 but with identical degrees of sulfation and sulfated cyclodextrin containing one or two sulfate groups per glucose unit, respectively.

A sugar backbone is not strictly needed for the antiviral activity of polysulfates, since sulfated polymers based on a polyacetal backbone, such as polyacetal polysulfate, or simply a carbon-carbon backbone, such as polyvinyl alcohol sulfate and its copolymer with acrylic acid have also proved to be highly-efficient anti-HIV agents in vitro, irrespective of their MW or degree of sulfation. This bodes well for melanins and their nonglycosidic backbones.

The 50% inhibitory concentration $IC_{50}$ for a number of polysulfated polysaccharides is shown in Table 1 to illustrate the effects of molecular weight and degree of sulfation. Data for two HIV strains are given (Witvrouw, R.;

Desmyter, J.;De Clercq, E., 1994 Antiviral Chem. Chemother. 5:345).

TABLE 1

Inhibitor Effects of Various Polysulfates on HIV Strains

| Compound | | HIV-1 (111a) | HIV-2 (ROD) |
|---|---|---|---|
| Linear | | | |
| Chemically-synthesized | | | |
| Dextran sulfate | (MW 1000) | 7.1 | 0.1 |
| | (MW 1500) | 2.9 | 0.1 |
| | (MW 3400) | 0.7 | 0.3 |
| | (MW 5000) | 0.5 | 0.3 |
| | (MW 10000) | 0.2 | 1.2 |
| | (MW 40000) | 0.4 | 2.3 |
| | (MW 70000) | 0.8 | 3.9 |
| | (MW 110000) | 0.6 | 4.1 |
| | (MW 500000) | 0.8 | 4.1 |
| Pentosan polysulfate | | 0.8 | 0.01 |
| Heparin | | 0.8 | 4.5 |
| Circular | | | |
| α-cyclodextrin hexasulfate | | 26.2 | 1.9 |
| β-cyclodextrin heptasulfate | | 3.0 | 1.8 |
| γ-cyclodextrin octasulfate | | 0.6 | 1.6 |
| α-cyclodextrin tetradecasulfate | | 0.8 | 1.0 |
| γ-cyclodextrin hexadecasulfate | | 0.2 | 0.4 |

Additional references to illustrate the anti-HIV activity of polysulfated polysaccharides include cyclodextrin sulfate (Moriya, T. et al., J. Med. Chem. 36:1674, 1993 and Uryu, T. et al., in Carbohydrates and Carbohydrate Polymers Analysis, Biotechnology, Modification, *Antiviral, Biomedical and Other Applications*, Yalpani, M., ed. Chapt. 10 ATL Press, 1993), curdlan sulfate (Uryu, T. op cit., and Osawa, Z. et al., *Carbohydrate Polymers* 21:283, 1993., lentinan sulfate (Uryu, T. op cit.), ribofuranan sulfate (Uryu, T., op cit.) pentosan polysulfate (Srivastava, A. K., et al., *Molec. Cell. Biochem.* 120:127, 1993), galactan sulfate and sulfated alkylmaltooligosaccharides.

Similar data exists for polysulfonated polymers (Tan, G. T. et al., *Biochem. Biophys. Acta.* 1181:183, 1993; Pivel R. et al., European Patent 0 49 1 644 A 2 Jun. 24, 1992 and Mohan, P., et al., *Drugs of the Future* 18:351, 1993). Natural and synthetic polysulfated and polysulfonated polysaccharides and other polymers offer strong in vitro anti-HIV activity and their inhibitory activity greatly exceeds that of control polymers not having polyanionic characteristics.

Polysulfated and polysulfonated melanins prepared as presently described are shown to possess superior anti-HIV activity as compared to unmodified melanins. Such compounds represent compositions of matter that have not been previously described or suggested in the published literature.

The preparation of melanins containing halogen atoms (fluorine, chlorine, bromine and iodine) provides melanin derivatives with increased biological activity. Generally, incorporation of a halogen atom into a molecule provides an activity amplification effect (S. L. Neidleman and J. Geigert. Biohalogenations: Principles, basic Roles and Applications. Ellis Horwood Ltd. Publishers, Chichester, England, 1986). Halogen incorporation into melanin may be accomplished in at least three ways: (1) The use of a halogenated tyrosine or tyrosine-containing peptide in the enzymatic or chemical synthesis of a melanin; (2) the enzymatic halogenation of a melanin with a haloperoxidase; and (3) chemical halogenations.

Sources of halogens or halogenation agents which may be used according to this invention include N-haloamides, e.g., N-halo (lower alkanoic acid amides) such as N-bromoacetamide, N-chloroacetamide, N-haloimides, e.g., N-halo (lower alkanadioic acid imides) such as N-bromosuccinimide, N-chlorosuccinimide, N-iodosuccinimide, or a halogenating enzyme such as chloroperoxidase, lactoperoxidase, bromoperoxidase and myeloperoxidase. All of these chemicals and enzymes are commercially available.

For the purposes of the present invention, melanins that have been modified to contain sulfate, sulfonyl, halogen groups, or a mixture thereof, shall contain between one modifying group and up to a substantially saturating quantity of modifying groups, preferably between one modifying group and about fifty percent saturation of the potential modification sites for a given group, and more preferably between at least about 3 modifying groups and up to about forty percent saturation of the potential modification sites for a given group or mixture of groups.

In addition, natural and synthetic polysulfated and polysulfonated polysaccharides and other polymers offer strong in vitro anti-HIV activity and their inhibitory activity greatly exceeds that of control polymers not having polyanionic characteristics. Polysulfated and polysulfonated melanins are prepared and shown to possess superior anti-HIV activity as compared to the unmodified melanins. These compounds are inherently innovative compositions of matter, which are generally characterized as possessing enhanced activity against HIV. For the purposes of the present invention, the term "enhanced anti-HIV activity" shall refer to any enzymatically synthesized or modified compound that displays a significant increase in anti-HIV activity relative to non-enzymatically synthesized or non-modified control compounds in an in vitro assay.

Further, it has also been demonstrated that features such as, but not limited to, oxidizing melanins with hydrogen peroxide; producing melanins within a particular molecular weight; and precipitating melanins with hydrochloric acid all contributed to improved biological activity against HIV.

Definitions

For purposes of this patent application the following definitions of terms are provided:

Tyrosinase. An enzyme that catalyzes oxidative polymerization of tyrosine and related phenolic compounds and forms melanin.

Melanin. A polyphenolic polymer derived from chemical or enzymatic polymerization of substrates including, but not limited to, tyrosine or tyrosine derivatives or tyrosyl-containing peptides.

Substrate. Mono- and ortho-diphenols (catechols) derived of bulky groups or crowded substituent patterns adjacent to the hydroxyl group(s) on the aromatic ring and combinations thereof. In addition, hydroquinones, hydroxybenzoquinone, benzoquinone and dibenzofuran are included as substrates.

Tyrosyl-containing peptides. Peptides containing a tyrosine amino acid.

Synthetic melanin. Melanins produced by highly concentrated tyrosinase preparations in conjunction with exogenously added substrates.

Pharmaceutical grade melanin. Purified melanin, or modified forms thereof, that is both substantially free of toxic agents, and of sufficient purity to be suitable for use in in vivo therapy.

For the purposes of the present invention, a composition having anti-HIV activity shall be defined as any composition having the property of being capable of inhibiting HIV replication by directly interfering with HIV-mediated processes; interfering with viral spread or host cell infection; advantageously modulating the immune response against HIV or any HIV related disease symptom; or otherwise beneficially effecting HIV infection, spread, or clearance in any way whatsoever.

Where the therapeutic use of the presently described melanins is contemplated, the melanins are preferably of pharmaceutical grade, and are administered in a pharmaceutically acceptable carrier, via oral, intranasal, rectal, topical, intraperitoneal, intravenous, intramuscular, subcutaneous, subdermal, transdermal, intrathecal methods, or the like. Typically, the preferred formulation for a given melanin composition is dependent on the location of the target cells in the host animal, or the locations in a host where HIV is known to initially invade or replicate.

Particularly where in vivo use is contemplated, the various biochemical components used to formulate the presently described melanins are preferably of high purity and are substantially free of potentially harmful contaminants (e.g., at least National Food (NF) grade, generally at least analytical grade, and preferably at least pharmaceutical grade). To the extent that a given compound must be synthesized prior to use, such synthesis or subsequent purification shall preferably result in a product that is substantially free of any potentially toxic agents, particularly endotoxins, which may have been used or present during the synthesis or purification procedures.

Where diagnostic, therapeutic or medicinal use of purified melanin, or derivatives thereof, is contemplated, the melanin may generally be prepared and maintained under sterile conditions that minimize that risk of, or avoid, microbial contamination. Because of the relatively small size and inherent stability of purified melanin, compositions comprising melanin may also be sterile filtered prior to use. In addition to the above methods of sterile preparation and filter sterilization, antimicrobial agents may also be added to the melanin compositions. Antimicrobial agents which may be used, generally in amounts of up to about 3% w/v, preferably from about 0.5 to 2.5%, of the total formulation, include, but are not limited to, methylparaben, ethylparaben, propylparaben, butylparaben, phenol, dehydroacetic acid, phenylethyl alcohol, sodium benzoate, sorbic acid, thymol, thimerosal, sodium dehydroacetate, benzyl alcohol, cresol, p-chloro-m-cresol, chlorobutanol, phenylmercuric acetate, phenylmercuric borate, phenylmercuric nitrate and benzylalkonium chloride. Preferably, antimicrobial additives will either enhance the biochemical properties of the melanin, or will be inert with respect melanin activity. To the extent that a given antimicrobial agent may prove deleterious to melanin activity, another agent may be substituted which effects the desired functions of melanin to a lesser extent.

One of ordinary skill will appreciate that, from a medical practitioner's or patient's perspective, virtually any alleviation or prevention of an undesirable symptom (e.g., symptoms related to the presence of HIV in the body) would be desirable. Thus, the terms "treatment", "therapeutic use", or "medicinal use" used herein shall refer to any and all uses of the claimed melanins which remedy a disease state or symptoms, or otherwise prevent, hinder, retard, or reverse the progression of AIDS, or a related illness, disease, or other undesirable symptom in any way whatsoever.

Preferably, animal hosts that may be treated using the melanins of the present invention include, but are not limited to SCID-HU mice, cats, primates, and particularly humans, or any naturally occurring animal or animal that has been engineered to be susceptible to infection by HIV or a related lentivirus.

When used in the therapeutic treatment of disease, an appropriate dosage of melanin, or a mixture thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken Phase I clinical studies in normal subjects help establish safe doses. Additionally, therapeutic dosages may also be altered depending upon factors such as, the concurrent use of other anti-AIDS pharmaceuticals (e.g., RT-inhibitors such as AZT and ddI, etc., and inhibitors of HIV protease activity), the time elapsed since the initial exposure to HIV, the state of AIDS progression, and the size or species of the host.

The presently described melanin compositions should preferably be parenterally administered at concentrations below the maximal tolerable dose (MTD) established for the melanin composition. For parenteral application by injection, melanins preparations may comprise an aqueous solution of a water soluble, or solubilized, and pharmaceutical grade melanin in an appropriately buffered saline solution. Injectable suspensions may also be prepared using appropriate liquid carriers, suspending agents, pH adjusting agents, isotonicity adjusting agents, preserving agents, and the like may be employed. Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference.

The presently described melanins, and modified forms thereof, may also be complexed with molecules that enhance their ability to enter the target cells. Examples of such molecules include, but are not limited to, carbohydrates, polyamines, amino acids, peptides, lipids, and molecules aiding nuclear transport. Additionally, the present demonstration of methods for chemically modifying melanins allows for the addition of agents that are capable of targeting specific tissues or cells. Examples of such targeting agents include, but are not limited to, cellular or viral receptors, ligands, antibodies, or aptameric oligonucleotides.

The following examples serve to more fully describe the manner of making and using the above-described melanins, as well as to set forth the best modes contemplated for carrying out various aspects of the invention. It is understood that these examples in no way serve to limit the true scope of this invention, but rather are presented solely for illustrative purposes.

6.0 EXAMPLES

6.1 Enzymatic Synthesis and Anti-HIV Testing of Various Melanins

Two grams of substrate (below) were dissolved in 100 ml of 25 mM sodium phosphate buffer, pH 7.0. The substrate solution was placed in a 250 ml flask, mixed using a rotary shaker at 300 rpm, and incubated at 30° C. Melanin synthesis was catalyzed by the addition of 4,000 dopachrome units of tyrosinase (produced as described in U.S. Pat. No. 5,340,734). Melanins were synthesized over a 40-hour period and recovered by lyophilization of the entire reaction mix.

L-dopa melanin was synthesized in water-soluble form as described. One gram of 1-dopa was dissolved in 400 ml of 0.025N NaOH and incubated for 2 days at room temperature with constant aeration. Aeration was accomplished with the aid of an air sparger using air that had been passed through a solution of 1N NaOH. Melanin was precipitated from the dark brown solution by adding 2 ml of concentrated HCl. The moist precipitate was collected by centrifugation, dissolved in 400 ml of deionized water, and precipitated again with 1 ml of concentrated HCl. The melanin was purified by a total of four precipitations, and then dissolved in 20 ml of 0.025 NaOH (the solution generally had a neutral pH after this step) and lyophilized. The final yield was 100 mg of a fine black powder which was soluble in phosphate buffered saline (PBS), pH 7.4 to at least 500 mg/ml.

Dried melanins were analyzed for anti-HIV activity essentially as described by Montefiori, et al., 1988, J. Clin. Microbiol. 26:231–235. In brief, the antiviral activities of the various melanins and melanin derivatives described in the present examples were measured in 96-well microdilution plates. Two-fold serial dilutions of melanins were made in triplicate in a total of 100 $\mu$l growth medium (RPMI-1640 containing 12% host-inactivated fetal bovine serum and 50 $\mu$g gentamicin/ml) per well. MT-2 cells ($5 \times 10^4$) in 100 $\mu$l of growth medium were added to each well and incubated for 10 minutes. Fifty microliters of virus ($5 \times 10^4$ $TCID_{50}$ /50 $\mu$l) were then added to all wells except for one row of eight noncytopathic control wells; these received growth medium in place of virus. Viral-induced cytopathic effect (CPE) was quantified three days later by vital dye (neutral red) uptake in remaining viable cells. Neutral red uptake is a linear function of cell viability with $A_{540}$ of 0.025 to 0.85 corresponding to $2 \times 10^4$ to $25 \times 10^4$ viable cells/well (Montefiori, et al., 1988). Percent protection is defined as the difference in $A_{540}$ between test wells (cells+melanin+virus) and virus control wells (cells+virus) divided by the difference in between cell control wells (cells only) and virus control wells.

The effective dose 50 (EC50, provided in $\mu$g/ml) denotes the initial concentration of melanin that provided protection to approximately fifty percent of the test cells and is generally indicative of the starting concentration of melanin (up to the MTD) that may be used to provide a therapeutic benefit. The therapeutic ratio was calculated by dividing the highest effective concentration of melanin that resulted in less than fifty percent cellular toxicity, by the EC50. Accordingly, the TR provides information about the general range of suitable therapeutic concentrations for a given melanin composition.

Both the EC50's and TR's for the various melanins synthesized in the following examples below were calculated with respect to a non-enzymatically produced control melanin (LD-10). LD-10 was prepared as described in U.S. Pat. No. 5,057,325, herein incorporated by reference:

TABLE 2

| Sample Preparation | Effective Dose 50 $EC_{50}$* | Therapeutic Ratio (TR) | LD-10 Control $EC_{50}$ | TR |
|---|---|---|---|---|
| Phe-Tyr | 7.0 | 7 | 2.0 | 25 |
| Tyr-Ala | 1.0 | 50 | 2.0 | 25 |
| Gly-Tyr/Tyr (5:1) | 1.5 | 29 | 2.0 | 25 |
| Tyr-Tyr | 1.1 | 45 | 2.0 | 25 |
| His-Tyr/Tyr (1:1) | 9.2 | 5 | 0.6 | 33 |
| Pro-Tyr/Tyr (2:1) | 1.0 | 50 | 0.6 | 33 |
| Chlorogenic acid/Tyr (1:0.5) | 0.5 | >100 | <0.4 | >88 |
| Glu-Tyr | 1.8 | 28 | 0.5 | 100 |

TABLE 2-continued

| Sample Preparation | Effective Dose 50 EC$_{50}$* | Therapeutic Ratio (TR) | LD-10 Control | |
|---|---|---|---|---|
| | | | EC$_{50}$ | TR |
| Gly-Tyr*** | >50 | 0 | 0.6 | 83 |
| Tyrosinase**** | >50 | 0 | 0.6 | 83 |

*Effective Dose 50 (in µg/ml)
**Therapeutic Ratio
***Gly-Tyr (Sigma Cat. No. G-3502, unreacted dipeptide).
****Tyrosinase: lyophilized preparation (20 dopachrome units/mg solid)

It is to be noted that not all dipeptide-derived melanins were superior to LD-10. The production of improved activity is selective. All gly-tyr were l-isomers, however, d-isomers have essentially the same activity.

6.2. Dipeptide Melanin Production

Dipeptide melanin was produced according to the methods presented in U.S. Pat. Nos. 5,466,592; 5,340,734 and 5,486,351, herein incorporated by reference. Glycine-tyrosine dipeptide melanin was synthesized in 2.0-liter jar fermentors. Ten grams of gly-tyr dipeptide (Sigma, G-3502) was dissolved in 1000 ml of 50 mM phosphate buffer (reaction mix pH 7.50). Gly-tyr melanin synthesis was catalyzed by the addition of 4,400 dopachrome units of tyrosinase (produced as described in U.S. Pat. No. 5,340,734). The reaction mixture was incubated at 30° C., 400 RPM and sparged using an air flow of 230 ml per minute for 24 hours. An additional 2,200 dopachrome units of tyrosinase was added after two hours of melanin synthesis.

Gly-tyr melanin was fractionated, concentrated and diafiltered through a series of Amicon, 10 sq. ft. spiral, regenerated cellulose membranes having molecular weight cut-offs of 10,000; 3,000 and 1,000 daltons. Membrane fractionated melanin was dried by lyophilization. A portion from each membrane fraction (e.g.,>10 kd, 3–10 kd, and 1–3) kd was further fractionated by HCl precipitation prior to lyophilization. Gly-tyr melanin was recovered by centrifugation (10,000×G for 15 min) after acid precipitation (by using HCl to reduce the reaction pH to about 1.5) and incubation at 4° C. for 24 hours. The acid-soluble melanin from each molecular weight fraction was recovered and dried by lyophilization.

TABLE 3

| Melanin Sample | Preparation | Anti-HIV-1 Effective Dose 50 | IIIB Activity Therapeutic Ratio |
|---|---|---|---|
| Experiment #1 | | | |
| AHM12 | 24-hour synthesis, 10.0 g/l substrate, >10 kd | 0.6 | 83 |
| AHM13 | >10 kd, HCl ppt, AHM12 | 0.4 | 125 |
| AHM14 | >10 kd, HCl soluble, AHM12 | 1.4 | 36 |
| AHM15 | 24-hour synthesis, 10.0 g/l substrate, 10–3 kd, HCl ppt | 0.6 | 83 |
| LD-10 | Control | 1.1 | 45 |
| Experiment #2 | | | |
| AHM17 | 24-hour synthesis, 10.0 g/l substrate 10–3 kd | 0.4 | 83 |
| AHM18 | 10–3 kd, HCl soluble, AHM17 | 1.0 | 50 |
| AHM19 | 24-hour synthesis, 10.0 g/l substrate, 3–1 kd | 1.5 | 33 |
| AHM20 | 3–1 kd, HCl ppt, AHM19 | 0.5 | 100 |
| AHM21 | 3–1 kd, HCl soluble, AHM19 | 1.3 | 38 |
| LD-10 | Control | 0.7 | 71 |

In each case, the HCl precipitated sample had higher anti-HIV activity than the starting fraction or the acid soluble fraction. The acid soluble fraction had lower activity than the starting material, and the higher molecular weight fractions had greater activity than the lower molecular weight fractions. The term "AHM" (see Table 3) denotes gly-tyr containing/derived melanin. Experiments #1 and #2 were each normalized to independently derived control values which were obtained using non-enzymatically derived melanin (LD-10).

6.3. Glycine-tyrosine Dipeptide Melanin: Large-Scale Synthesis and Polymer Fractionation and Recovery Glycine-tyrosine dipeptide melanin was synthesized in 2.0-liter jar fermentors. Five grams of gly-tyr dipeptide (Sigma, G-3502) was dissolved in 950 ml of 50 mM phosphate 35 buffer (reaction mix pH 7.00–7.15). Gly-tyr melanin synthesis was catalyzed by the addition of 7,500 dopachrome units of tyrosinase (produced as described in U.S. Pat. No. 5,340,734). Reaction mixtures were incubated at 30° C., 400 rpm and sparged with 230 ml air per minute for 3 to 22 hours.

Gly-tyr melanin was recovered by centrifugation (10,000×G, 15 minutes) after acid precipitation (reaction pH reduced to pH 1.5 by the addition of HCl) and incubation at 4° C. for 1 hour. Acid-precipitated melanin was dried by lyophilization.

Alternatively, gly-tyr melanin was fractionated, concentrated and diafiltered through Amicon, 10 sq. ft. spiral, regenerated cellulose membranes having molecular weight cut-offs of either 10,000 or 1,000 daltons. Membrane fractionated melanin was dried by lyophilization. Melanins were analyzed for anti-HIV activity as described above.

TABLE 4

| Activity Sample | Preparation | Anti-HIV-1 Effective Dose 50 | IIIB Therapeutic Ratio |
|---|---|---|---|
| gly-tyr | 3-hour synthesis, 10–1 kd | 0.9 | 56 |
| gly-tyr | 22-hour synthesis, 10–1 kd | 0.8 | 63 |
| gly-tyr | 3-hour synthesis, >10 kd | 0.4 | >125 |
| gly-tyr | 22-hour synthesis, >10 kd | <0.4 | >125 |
| gly-tyr | 3-hour synthesis pH 1.5, HCl precipitate | <0.4 | >125 |
| Control | LD-10 | 0.7 | 46 |

6.4. Preparation Of Gly-Tyr Melanin Using An FPLC Purified, High Specific Activity Tyrosinase (920 Dopachrome Units/Mg Protein)

Glycine-tyrosine dipeptide melanin was synthesized in a 2.0-liter jar fermentor. Ten grams of gly-tyr dipeptide (Sigma, G-3502) was dissolved in 1000 ml of 30 mM $Na_2HPO_4$ buffer (reaction mix pH 7.55). Gly-tyr melanin synthesis was catalyzed by the addition of 9,300 dopachrome units of high specific activity (920 units/mg protein) tyrosinase purified by FPLC. Tyrosinase was added over a two-hour period while the concentration of dissolved oxygen was kept at approximately 50%. The pH was maintained at about 7.0–7.1 by the addition of NaOH. The reaction mixture was incubated at 30° C., 500 rpm and sparged with 500 ml air per minute for 2.5 hours.

Immediately after synthesis, the gly-tyr melanin was fractionated, concentrated and diafiltered through an Amicon, 10 sq. ft. spiral, regenerated cellulose membranes having molecular weight cut-offs of 10,000; 3,000 and 1,000 daltons. Membrane fractionated melanin was dried by lyophilization and analyzed for anti-HIV activity as described.

TABLE 5

| Melanin Sample | Preparation | Anti-HIV-1 Effective Dose 50 | IIIB Activity Therapeutic Ratio |
|---|---|---|---|
| AHM 40 | HCl ppt | 0.6 | 83 |
| AHM 41 | >10 kd | 0.45 | 111 |
| LD-10 | Control | 0.9 | 56 |

Note:
AHM denotes gly-tyr derived melanin.

6.5. Production of Polysulfated Melanins

Melanin (1 gm) is stirred in 50 ml DMF for 12 hours at room temperature. Then, $SO_3$ DMF complex (1:2 molar ratio) is added, stirred at room temperature for about one to four hours; then, at 70° C. for 30 minutes. The levels of sulfation may be controlled by varying reaction time. After the reaction, the slurry is poured into 200 ml water, neutralized with 1N sodium hydroxide solution and precipitated in methanol in a total volume of 1.2 liters. The precipitate is redissolved in 300 ml water and dialyzed against water for about five days. The insoluble portion is collected by centrifugation. The solution is concentrated and freeze-dried. Anti-HIV activity is analyzed as described. Melanins polysulfated include those enzymatically and non-enzymatically produced from l-tyrosine, gly-tyr, tyr-tyr and tyr-ala with varying molecular weights and oxidation by hydrogen peroxide. The anti-HIV activity of all melanins is improved by polysulfonation. Anti-HIV activity expected to be inherent in such modified melanins is presented in Table 6.

TABLE 6

| | Untreated | | Polysulfated Reaction time | | |
|---|---|---|---|---|---|
| Substrate | ($EC_{50}$) | (TR) | Hrs | ($EC_{50}$)* | (TR)* |
| l-tyrosine | 4.0 | 12 | 1.5 | 3.0 | 18 |
| | | | 4.5 | 2.0 | 25 |
| gly-tyr | 1.0 | 50 | 1.5 | 0.8 | 70 |
| | | | 4.5 | 0.6 | 90 |
| tyr-tyr | 1.1 | 45 | 1.5 | 0.8 | 70 |
| | | | 4.5 | 0.6 | 90 |
| tyr-ala | 1.1 | 50 | 1.5 | 0.8 | 70 |
| | | | 4.5 | 0.6 | 90 |

TABLE 6-continued

| | Untreated | | Polysulfated Reaction time | | |
|---|---|---|---|---|---|
| Substrate | ($EC_{50}$) | (TR) | Hrs | ($EC_{50}$)* | (TR)* |
| LD-10 | 2.0 | 25 | 1.5 | 1.5 | 36 |
| | | | 4.5 | 1.2 | 45 |

*Effective Dose 50
**Therapeutic Ratio

6.6. Alternate Production of Polysulfated Melanine

Melanin (3 gm) is treated with triethylamine-sulfonic acid in dimethylformamide (DMF) at 0° C. for 5, 10 and 20 hours to allow for varying levels of sulfation. The material is then treated with sodium bicarbonate to give 5.1 gm sodium melanin polysulfate. Anti-HIV activity is analyzed as described. Melanins polysulfated include those of example 7. The anti-HIV activity of all melanins is improved by polysulfation. Representative data of the anti-HIV activity respected by such melanins is presented in Table 7.

TABLE 7

| | Untreated | | Polysulfated Reaction time | | |
|---|---|---|---|---|---|
| Substrate | ($EC_{50}$)* | (TR)** | (Hrs) | ($EC_{50}$) | (TR) |
| l-tyrosine | 4.0 | 12 | 5 | 3.0 | 18 |
| | | | 10 | 2.0 | 25 |
| | | | 20 | 1.8 | 28 |
| gly-tyr | 1.0 | 50 | 5 | 0.8 | 70 |
| | | | 10 | 0.6 | 90 |
| | | | 20 | 0.5 | 100 |
| tyr-tyr | 1.1 | 45 | 5 | 0.8 | 70 |
| | | | 10 | 0.6 | 90 |
| | | | 20 | 0.5 | 100 |
| tyr-ala | 1.1 | 50 | 5 | 0.8 | 70 |
| | | | 10 | 0.6 | 90 |
| | | | 20 | 0.5 | 100 |
| LD-10 | 2.0 | 25 | 5 | 1.5 | 36 |
| | | | 10 | 1.2 | 45 |
| | | | 20 | 1.0 | 50 |

*Effective Dose 50
**Therapeutic Ratio

6.7. Alternative Production of Polysulfonated Melanine

Melanin is dissolved in 10–50 mM sodium periodate to a final concentration of 0.5–4 gm per liter and incubated in the dark at room temperature for 2–7 days to allow for varying levels of sulfonation. The oxidized product is dialyzed against running water for about 24 hours. The product is then lyophilized. The material is then dissolved in water in a lidded container at 0.5–4 g per liter and the pH is adjusted to about 6.5–8.5 A solution of cysteic acid (at a concentration of 5–10 g per liter with pH adjusted to 6.5–8.5 ) is added to the reaction mixture until cysteic acid is present in a molar ration of between about 0.5–2.0 relative to the number of aldehyde groups present in the melanin. The mixture is incubated at about 95–100° C. until the cysteic acid is consumed or the concentration of cysteic acid remains stable. The material is then dialyzed against running water and lyophilized. Anti-HIV activity was analyzed as described. The anti-HIV activity expected by such modified melanins is presented in Table 8.

TABLE 8

| Substrate | Untreated | | Polysulfated Reaction time | | |
|---|---|---|---|---|---|
| | (EC$_{50}$)* | (TR)** | (Hrs) | (EC$_{50}$) | (TR) |
| l-tyrosine | 4.0 | 12 | 2 | 3.0 | 18 |
| | | | 7 | 1.8 | 28 |
| gly-tyr | 1.0 | 50 | 2 | 0.8 | 70 |
| | | | 7 | 0.5 | 100 |
| tyr-tyr | 1.1 | 45 | 2 | 0.8 | 70 |
| | | | 7 | 0.5 | 100 |
| tyr-ala | 1.1 | 50 | 2 | 0.8 | 70 |
| | | | 7 | 0.5 | 100 |
| LD-10 | 2.0 | 25 | 2 | 1.5 | 36 |
| | | | 7 | 1.0 | 50 |

*Effective Dose 50
**Therapeutic Ratio

6.8. Preparation of Blue to Blue-Green Melanins

Upon incomplete or altered synthesis of gly-tyr substrate due to limiting tyrosinase, excess substrate, limiting oxygen or non-optimal pH conditions, a blue to blue-green melanin is formed rather than red to red-brown gly-tyr melanin. The blue/green gly-tyr melanin has a unique absorbance peak at 605 nm and exhibits decreased anti-HIV activity compared to the red/brown gly-tyr melanin product. See Table 9 and FIG. 1.

Blue/green glycine-tyrosine melanin was produced via synthesis in an unbuffered reaction mix. Ten grams of gly-tyr dipeptide (Sigma Cat No. 3502) was dissolved in 950 ml of deionized water (reaction mix pH 5.42). The reaction mix was adjusted to a pH of 7.53 by the addition of NaOH. Gly-tyr melanin synthesis was catalyzed by the addition of 6,000 dopachrome unites of high specific activity (920 units/mg protein) tyrosinase purified by FPLC. The reaction mixture was incubated at 30° C., 500 rpm and sparged with 500 ml air per minute for 3 hours. NaOH was added to the reaction mix to keep the pH above 5.6. Since the reaction was unbuffered, the pH varied widely between 7.53 and 5.64. The dark red reaction mix was incubated at 4° C. for 1.5 hours. During the 1.5 hour incubation, the red gly-tyr melanin solution changed to a blue/green color. Spectral analysis of the blue/green melanin reaction mixture indicated the presence of a large quantity of unreacted substrate.

The blue/green gly-tyr melanin was fractionated, concentrated and diafiltered through a series of Amicon, 10 sq ft spiral, regenerated cellulose membrane having molecular weight cut-offs of 10,000; 3,000 and 1,000 daltons. Membrane fractionated melanin was dried by lyophilization and analyzed for anti-HIV activity as described (Montefiori, et al., op cit.).

Red/brown glycine-tyrosine melanin was produced via synthesis in a phosphate buffered reaction mix. Ten grams of gly-tyr dipeptide and 4.26 grams of Na$_2$HPO$_4$ were dissolved in 950 ml of deionized water (reaction mix pH 7.55). Gly-tyr melanin synthesis was catalyzed by the addition of 9,300 dopachrome units of high specific activity (970 units/mg protein) tyrosinase purified by FPLC. The reaction mixture was incubated at 30° C., 500 rpm and sparged with 500 ml air per minute for 3 hours. The buffered reaction was maintained at a pH of 7.55 to 7.01 by the addition of NaOH.

Immediately after synthesis, the red/brown gly-tyr melanin was fractionated, concentrated and diafiltered through a series of Amicon, 10 sq ft, spiral, regenerated cellulose membranes having molecular weight cut-offs of 10,000; 3,000 and 1,000 daltons. Membrane fractionated melanin was dried by lyophilization and analyzed for anti-HIV activity as described.

TABLE 9

| Sample | Preparation | Anti-HIV-1 Effective Dose 50 | IIIB Activity Therapeutic Ratio |
|---|---|---|---|
| AHM42 | >10 kd, "red" | 0.68 | 74 |
| AHM43 | >10 kd, "blue-green" | 2.0 | 25 |
| AHM44 | 10-3 kd, "red" | 2.0 | 25 |
| AHM45 | 10-3 kd, "blue-green" | 2.5 | 20 |
| AHM46 | 3-1 kd, "red" | 2.5 | 20 |
| AHM47 | 3-1 kd, "blue-green" | 13.0 | 4 |
| LD-10 | Control | 0.9 | 56 |

Note:
"AHM" denotes gly-tyr derived melanin.

6.9. Chemical Modification Using Oxidants

Chemically-modified melanins can be obtained by oxidizing melanin with oxidants such as, but not limited to, hydrogen peroxide and hypochlorite. For example, l-tyrosine-derived melanin (which is black in color) can be modified to a lighter color by hydrogen peroxide. The final color of melanin is a function of the solution pH, the concentration of hydrogen peroxide used and the length of time the melanin is oxidized. The rate of melanin oxidation can be followed spectrophotometrically. Hydrogen peroxide can then be removed by ultrafiltration or passage of the reaction mixture through a catalyst such as platinum.

6.10. In Vitro Synthesis Production of Melanin in Aqueous Solution

L-tyrosine melanin was synthesized in vitro with the Streptomyces tyrosinase as described in U.S. Pat. Nos. 5,466,592; 5,340,734; and 5,486,351. A 3.0 liter reaction containing 30 g l-tyrosine, 2610 ml 0.05M Na$_2$HPO$_4$, pH 8.3, and 90 ml ultra-filtered Streptomyces tyrosinase (40,500 dopachrome units) was performed in a 6.0-liter Wheaton Proteus integral fermentor. The melanin synthesis was carried out at 30° C., 400 rpm, and 1 liter per minute air flow supplemented with 60 ml of oxygen per minute. The rpms were increased to 500, after 1 hour. Additional diafiltered tyrosinase was added at 2 hours, (20,250 units), 3.25 hours, (5,400 units), and at 3.5 hours, (20,250 units). A final of 2,880 units tyrosinase per gram l-tyrosine was achieved by this enzyme addition scheme. The rate of melanin synthesis was followed by monitoring the increase in absorbency at 400 nm. An average rate of melanin synthesis of 1.76 g melanin/hour was obtained in this reaction. Melanin synthesis was determined to be complete after about 6 hours when there was no significant increase in the OD$_{400}$. Melanin was isolated after in vitro synthesis by reducing the pH of the reaction mixture to below 4.0 with HCl, and recovering the precipitated melanin by centrifugation. The sample was dried by lyophilization and then analyzed for anti-HIV activity as described.

The melanin produced as described above was chemically modified by oxidation with hydrogen peroxide. In brief, 30% hydrogen peroxide was added to 3 liters of in vitro synthesized l-tyrosine melanin (in a 6-liter Wheaton Proteus integral fermentor), until a final concentration of about 3.3% hydrogen peroxide was obtained. The melanin was oxidized at 30° C. and 350 RPM. The chemically oxidized melanin was recovered at various time points by acid precipitation, centrifugation, and drying. The pH of the oxidized melanin solution was reduced to below pH 2.5 by the addition of concentrated HCl. The acidified melanin was placed at 4° C. for 17 hours to facilitate precipitation. The precipitated melanin was then recovered by centrifugation @ 7,000×G for 10 minutes. Residual amounts of hydrogen peroxide were removed by drying the melanin at 65° C. Melanin was removed from the reaction mixture at various times and was analyzed spectrophotometrically.

In the above example, hydrogen peroxide may also be removed from the reaction mixture by ultra-filtration through molecular weight cut-off filters. Using such a method, the oxidized melanin may be removed at the same time that specific size fractions of melanin are isolated.

TABLE 10

| Sample Preparation | Effective Dose 50 ($EC_{50}$) | Anti-HIV-1 Therapeutic Ratio (TR) | IIIB Activity LD-10 Control $EC_{50}$ | TR |
| --- | --- | --- | --- | --- |
| l-tyrosine melanin | 4 | >12 | 0.4 | 85 |
| l-tyrosine melanin, hydrogen peroxide treated | 0.8 | 63 | 0.3 | 40 |
| l-tyrosine melanin hydrogen peroxide oxidized, <3 kd | 2.2 | 18 | 0.3 | 40 |

The synthesized melanin was oxidized for 24 hours and then size fractionated by ultrafiltration through both 30 kd and 3 kd molecular weight cut-off regenerated cellulose filters. The oxidized melanins have a much higher solubility in aqueous solution at neutral pH as compared to 1-tyrosine melanin.

6.11. Chemical Production of Halogenated Melanins

Halogenated melanins are produced by adding 500 mg of N-bromosuccinimide to melanin (1 g) dispersed in an aqueous solution buffered at pH 4.0 using 0.3 M potassium phosphate. The solution is stirred for 2 hours and is then dialyzed for 6 hours against running water, followed by lyophilization. Anti-HIV activity is determined as described. Expected activity of melanins is presented in Table 11.

TABLE 11

| | Untreated | | Polyhalogenated Reaction time | |
| --- | --- | --- | --- | --- |
| Substrate | ($EC_{50}$)* | (TR)** | ($EC_{50}$) | (TR) |
| l-tyrosine | 4.0 | 12 | 2.0 | 25 |
| gly-tyr | 1.0 | 50 | 0.6 | 90 |
| tyr-tyr | 1.1 | 45 | 0.6 | 90 |
| tyr-ala | 1.1 | 50 | 0.6 | 90 |
| LD-10 | 2.0 | 25 | 1.2 | 45 |

*Effective Dose 50
**Therapeutic Ratio

6.12. Enzymatic Production of Haloaenated Melanins

One gram of melanin is suspended in aqueous solution buffered at pH 4.0 using 0.3 M potassium phosphate. The melanin solution is then combined with 1,250 units of chloroperoxidase (Sigma Cat. No. 0887). The solution is stirred for about 6 hours, dialyzed for another 6 hours against running water. and then lyophilized. As an additional control, a corresponding solution without melanin is treated likewise. Anti-HIV activity is determined as described. Expected activity of melanins is presented in Table 12.

TABLE 12

| | Untreated | | Polyhalogenated Reaction time | |
| --- | --- | --- | --- | --- |
| Substrate | ($EC_{50}$)* | (TR)** | ($EC_{50}$) | (TR) |
| l-tyrasine | 4.0 | 12 | 2.0 | 25 |
| gly-tyr | 1.0 | 50 | 0.6 | 90 |
| tyr-tyr | 1.1 | 45 | 0.6 | 90 |
| tyr-ala | 1.1 | 50 | 0.6 | 90 |
| LD-10 | 2.0 | 25 | 1.2 | 45 |
| None | >50 | 0 | >50 | 0 |

*Effective Dose 50
**Therapeutic Ratio

Although non-enzymatically produced melanins have been shown to possess anti-HIV activity, the enzymatic production of melanin allows for the generation of novel melanin compositions using defined substrates, and novel combinations thereof. Additionally, such melanins are well suited to derivatization by addition of, for example, polysulfates and polysulfonates. The presently disclosed methods of producing, purifying, and fractionating melanin, and modified forms thereof, have resulted in new melanin compositions with improved anti-HIV activity relative to melanins synthesized using non-enzymatic methods (such as the LD-10). However, as demonstrated by the present disclosure, not all dipeptide-derived melanins are superior to LD-10, and only certain of the presently disclosed melanins possess this unexpected property.

EQUIVALENTS

The foregoing specification is considered to be sufficient to enable one skilled in the art to broadly practice the presently described invention. Indeed, various modifications of the above-described methods for carrying out the invention which are obvious to those skilled in the field of microbiology, biochemistry, organic chemistry, medicine or related fields are intended to be within the scope of the following claims. All patents, patent applications, and publications cited are incorporated herein by reference.

What is claimed is:

1. A method for treating HIV infection, comprising administrating a therapeutically effective dose of melanin wherein said melanin is synthesized by chemical or enzymatic methods and contains at least one anionic group selected from the group consisting of sulfates and sulfonyls.

2. The method according to claim 1, wherein a high-specific activity tyrosinase is used to enzymatically synthesize said melanin.

3. The method according to claim 1, in which said melanin is enzymatically synthesized using a tyrosine-containing substrate selected from the group consisting of mono-diphenol, ortho-diphenol, hydroquinone, hydroxybenzoquinone, benzoquinone, dibenzofuran, tyrosine, glycine-tyrosine, tyrosine-alanine, and tyrosine-tyrosine.

4. The method according to claim 3, wherein said substrate comprises chlorogenic acid and tyrosine.

5. The method according to claim 3, wherein said substrate is tyrosine.

6. The method according to claim 3, wherein said substrate is mono-diphenol.

7. The method according to claim 3, wherein said substrate is ortho-diphenol.

8. The method according to claim 3, wherein said substrate is hydroquinone.

9. The method according to claim 3, wherein said substrate is hydroxybenzoquinone.

10. The method according to claim 3, wherein said substrate is benzoquinone.

11. The method according to claim 3, wherein said substrate is dibenzofuran.

12. The method according to claim 3, wherein said substrate is glycine-tyrosine.

13. The method according to claim 3, wherein said substrate is tyrosine-alanine.

14. The method according to claim 3, wherein said substrate is tyrosine-tyrosine.

15. The method according to claim 3, wherein said melanin is further modified by chemical oxidation.

16. The method according to claim 15, wherein said chemical oxidation is carried out by hydrogen peroxide.

17. The method according to claim 15, wherein said chemical oxidation is carried out by hypochlorite.

18. The method according to claim 3, wherein said melanin is further purified by reducing the pH of a solution containing said melanin to less than 7.0.

19. The method according to claim 18, wherein said pH is less than about 4.

20. The method according to claim 19, wherein said pH is about 1.5.

21. The method according to claim 1, wherein said melanin contains at least one sulfonyl group.

22. The method according to claim 1, wherein said melanin contains at least one sulfate group.

23. The method according to claim 1, wherein said melanin comprises a dipeptide substrate and one or more chemical groups selected from the group consisting of sulfonyls and sulfates.

24. The method according to claim 23, wherein said dipeptide substrate is glycine-tyrosine.

25. A method of treating AIDS, comprising administrating a therapeutically effective dose of melanin, wherein said melanin contains at least one sulfate group or one sulfonyl group.

26. The method according to claim 25, wherein said melanin is made from a dipeptide substrate.

27. The method according to claim 25, wherein said melanin is made from dipeptide and tyrosine substrates.

28. The method according to claim 27, wherein said dipeptide is glycine-tyrosine.

29. The method according to claim 25, wherein said melanin contains sulfonyl groups.

30. The method according to claim 25, wherein said melanin contains sulfate groups.

* * * * *